United States Patent [19]

Yudovich et al.

[11] 4,379,025

[45] Apr. 5, 1983

[54] WATER REMOVAL FROM BUTYLENE OXIDES BY LIQUID EXTRACTION WITH SELECTED EXTRACTIVE SOLVENTS

[75] Inventors: Amos Yudovich, Tulsa, Okla.; Norman H. Sweed, Berkeley Heights, N.J.

[73] Assignee: Atlantic Richfield Company, Los Angeles, Calif.

[21] Appl. No.: 381,122

[22] Filed: May 24, 1982

[51] Int. Cl.³ .................. B01D 3/40; C07D 301/32
[52] U.S. Cl. ...................................... 203/14; 203/43; 203/70; 549/541
[58] Field of Search .............................. 203/14, 43–46, 203/70; 549/529, 541

[56] References Cited

U.S. PATENT DOCUMENTS

| | | | |
|---|---|---|---|
| 2,779,721 | 1/1957 | Houtman et al. | 203/14 |
| 2,903,465 | 9/1959 | Suter et al. | 203/70 |
| 3,039,940 | 6/1962 | Prinz et al. | 203/70 |
| 3,338,800 | 8/1967 | Binning et al. | 203/70 |
| 3,464,897 | 9/1969 | Jubin | 549/541 |
| 3,523,956 | 8/1970 | Kaplan | 549/529 |
| 3,607,669 | 9/1971 | Jubin | 203/14 |
| 3,654,317 | 4/1972 | Harrod et al. | 549/529 |
| 3,843,488 | 10/1974 | Schmidt | 203/70 |
| 4,113,747 | 9/1978 | Prescher et al. | 549/541 |

*Primary Examiner*—Wilbur L. Bascomb, Jr.
*Attorney, Agent, or Firm*—Craig E. Larson

[57] ABSTRACT

A process for removing water from butylene oxides which comprises liquid extraction of crude butylene oxides with a solvent comprising acyclic, paraffinic hydrocarbons having from 7 to 9 carbon atoms per molecule.

8 Claims, No Drawings

WATER REMOVAL FROM BUTYLENE OXIDES BY LIQUID EXTRACTION WITH SELECTED EXTRACTIVE SOLVENTS

BACKGROUND OF THE INVENTION

1. Field of the Invention

This invention relates to a method of removing water from butylene oxides. More particularly, this invention relates to drying 1,2-butylene oxide; cis- or trans-2,3-butylene oxide; isobutylene oxide; or mixtures thereof. This invention also relates to a process for removing impurities from butylene oxides by subjecting a crude butylene oxide stream, which cannot be easily purified by conventional distillation processes, to liquid extraction with suitable solvents. This invention still further relates to the resolution of crude 1,2-butylene oxide-containing mixtures produced by the epoxidation of 1-butylene by an organic hydroperoxide.

2. Description of the Prior Art

Alkylene oxides may be prepared from olefins by direct oxidation with oxygen; by oxidation with an oxidizing agent such as hydrogen peroxide, peracetic acid, or an organic hydroperoxide; or by conversion of halohydrins (prepared from the olefins) by the action of the base. Alkylene oxides are useful as polymerizable monomers, but they must be in a highly pure form for this purpose.

Alkylenes oxides obtained by direct oxidation or by oxidation with an oxidizing agent contain impurities including water and oxygen-containing organic compounds such as aldehydes, ketones, esters, alcohols, inorganic esters. Suggested methods for removing impurities include distillation (as well as extractive distillation) and chemical treatments. An example of the latter method is hydrolysis of esters and neutralization of acids with an alkali solution followed by distillation. Chemical treatments are generally undesirable because of associated product losses.

Purification of butylene oxides by means of distillation alone is difficult because of close-boiling impurities and formation of azetropic mixtures. Unlike ethylene or propylene oxides, butylene oxides form azetropes with water at atmospheric pressure. These azetropics are not readily separable by fractional distillation. Therefore, purification methods used in ethylene oxide and propylene oxide processes are not necessarily applicable to the purification of butylene oxide.

U.S. Pat. No. 2,779,721 suggests drying wet butylene oxides by liquid extraction of butylene oxide with a strong aqueous solution of an alkali metal hydroxide at a temperature below about 50° C. Up to 87% of the water can be removed from the mixture of butylene oxides containing 80% 1,2-butylene oxide and 2.3% water by this method. On the one hand, drying butylene oxide containing as little as 3.5% water by fractionation is impracticable since at least half of the oxide distills as the azeotrope before the water is removed. On the other hand, removal of water by fractionation is said to be practicable when the butylene oxide contains less than about 0.5 weight % water. Under these latter conditions, water is removed as an azeotrope containing 7% water and 93% oxide, leaving the remaining oxide dry. Because the isobutylene oxide/water azeotrope distills at lower temperatures than the water azeotropes of straight chain butylene oxides, the '721 patent further suggests that isobutylene oxide may be advantageously separated from straight chain butylene oxides by azeotropic distillation of the raffinate from the alkaline metal hydroxide extraction step. The patent teaches that the azeotropic column should be a still column having a large number of theoretical plates and that the separation be carried out under a high reflux ratio.

U.S. Pat. No. 3,338,800 teaches extractive distillation of olefin oxides having from 3 to 18 carbon atoms with a paraffin or paraffin naphtha solvent. More particularly, this patent suggests that oxygenated impurities boiling within 5° C. of the olefin oxide may be separated by extractive distillation using as solvents acyclic paraffinic hydrocarbons having boiling points at least 35° C. above the boiling points of the said purities. The problem addressed by this patent is that epoxide fractions produced by the direct oxidation of ethylenically unsaturated compounds with molecular oxygen in the liquid phase contain oxygenated impurities which, because their boiling points are similar to the desired epoxide product, cannot be separated by conventional distillation techniques. The impurities generally include acids, alcohols, aldehydes, ketones and esters. Example 3 of the patent shows extractive distillation of a crude mixture containing 85 weight % isobutylene oxide, 5 weight % ethyl formate and 10 weight % prionaldehyde with an n-octane solvent. The molar ratio of isobutylene oxide: n-octane was 1:11.5 in this example. The overhead temperature was 62° C. and the reboiler temperature was 108° C. Reflux ratio was 40:1. Also see U.S. Pat. No. 3,337,425 which teaches a process similar to the '800 patent except that olefinic naphtha and aromatic hydrocarbons having boiling points at least 35° C. above the impurities are employed as the extractive distillation agent.

U.S. Pat. No. 3,578,568 suggests purifying $C_3$–$C_5$ monoepoxides by extractive distillation with ethylene glycol, propylene glycol, ethylene glycol monomethylether or diethylene glycol monomethylethers.

U.S. Pat. No. 3,838,020 teaches a process for purifying $C_3$–$C_5$ alkylene oxides by extractive distillation using a mixed extractive solvent consisting of at least one solvent selected from the group consisting of 1,3-butylene glycol; 1,4-butylene glycol; isobutylene glycol and glycerine and at least one solvent selected from the group consisting dioxane, butylacetate and 2-ethylhexanol. The method is said to be suitable for purifying crude alkylene oxide streams containing up to about 5 weight % impurities.

An object of the present invention is an improved method for drying butylene oxides, especially straight-chain butylene oxides and particularly 1,2-butylene oxide. A further object of this invention is an improved method for purifying 1,2-butylene oxide produced by epoxidation of 1-butene with an organic hydroperoxide in the presence of the catalyst. Other objects will be apparent from the following description of the invention.

SUMMARY OF THE INVENTION

It is now been found that water and some water-soluble impurities may be removed from crude butylene oxides by liquid extraction using an acyclic, paraffinic hydrocarbon solvent having 7 to 9 carbon atoms. The solvent extracts butylene oxides from the crude solution, leaving an aqueous layer consisting of water and some water-soluble impurities. It has been found that 70–90% of the water present in the crude butylene oxide is readily removed by the method of this invention. Solvent to butylene oxide molar ratios are within the range from about 1 to 4:1, preferably from about 1 to 2:1. Solvent to butylene oxide ratios greater than about 2:1 do not appreciably increase the amount of water removed.

In a particular embodiment of this invention, high purity 1,2-butylene oxide is recovered from a crude, water-containing fraction obtained in processes wherein 1-butene is reacted with an organic hydroperoxide in the presence of a suitable catalyst.

DETAILED DESCRIPTION OF THE INVENTION

The "butylene oxides" treated in accordance with the method of this invention are those in which the oxygen atom is bonded to each of two contiguous carbon atoms. Thus, the term includes 1,2-butylene oxide, cis- and trans-butylene oxide and isobutylene oxide. Tetrahydrofuran is not a "butylene oxide" within the meaning of the present invention. In a preferred embodiment, the method of this invention is used to remove water from crude 1,2-butylene oxide streams.

The term "liquid extraction" is used herein to refer to the separation of two miscible liquids by the use of a solvent which preferentially dissolves one of them. In the context of the present invention, the liquids to be separated are butylene oxides and water. The solvent employed in the method of this invention preferentially dissolves the butylene oxides. Any known extraction equipment may be employed to carry out the liquid extraction method of this invention although simple, single-stage mixer-settler apparatus is preferred.

The present invention is broadly applicable to the resolution of mixtures containing butylene oxides and water. The amount of water present is not critical but generally the crude mixture will contain from about 2 to 5 weight % water and from about 92 to 96 weight % butylene oxide. Other impurities may also be present and will typically comprise higher- and lower-boiling oxygenated impurities.

The invention is applied with particular advantage to the recovery of high purity 1,2-butylene oxide from crude mixtures thereof obtained from processes wherein 1-butene is reacted with an organic hydroperoxide in the presence of a suitable catalyst. Such processes are known, having been described in various patents including U.S. Pat. Nos. 3,468,099 and 3,375,462. Olefins are epoxidized to form the corresponding oxirane derivative and the organic hydroperoxide is converted to the corresponding alcohol. The effluent from the reactor is processed by distillation or other methods to recover the olefin oxide and the by-product alcohol. Examples of these separation methods are described in U.S. Pat. Nos. 3,427,299 and 3,523,956.

The crude 1,2-butylene oxide mixture charged to the preferred embodiment of this invention comprises the mixture obtained by subjecting the total reaction product from the 1-butene oxidation reaction to such known treatments to effect removal of catalyst entrained from the epoxidation zone, unreacted 1-butene and the alcohol corresponding to the organic hydroperoxide. The organic hydroperoxide preferably employed in the epoxidation step is tertiary butyl hydroperoxide.

The principal impurities present in crude butylene oxide streams obtained in such processes are water, acetone, methanol, methyl acetate, ethyl acetate, methyl ethyl ketone, trans-2,3-butylene oxide and isobutylene oxide. Application of the present invention to such a stream results in substantial removal of water and methanol in the aqueous raffinate phase and substantially complete recovery of butylene oxide in the organic extract phase. Further distillative treatment of the organic extract produces a high-purity butylene oxide product.

The method of this invention is carried out by intimately contacting in the liquid phase a crude butylene oxide with a liquid solvent selected from the group consisting of acyclic, paraffinic hydrocarbons having from 7 to 9 carbon atoms to form a liquid/liquid dispersion, subjecting the liquid phase dispersion to quiescent conditions to effect separation of the two liquid phases, and separately recovering the aqueous phase raffinate and the organic phase extract. Solvent may be recovered for reuse from the extract by simple fractionation.

The liquid/liquid extraction may be performed batchwise or continuously, but preferably is performed continuously. Since the process is carried out in the liquid phase, the temperature in the liquid/liquid extraction zone is necessarily limited by the boiling point of butylene oxide at the pressure employed. Atmospheric or slightly greater pressures are preferred.

In a preferred embodiment of this invention, the butylene oxide phase recovered by liquid extraction is purified according to the teachings of concurrently filed U.S. patent application Ser. No. 381,121 entitled "Purification Of Butylene Oxides By Extractive Distillation With Selected Extractive Distillation Solvents", the contents of said application being incorporated herein by reference. This copending application teaches purification of butylene oxides (especially 1,2-butylene oxide) by a process comprising extractive distillation with acyclic, paraffinic hydrocarbons having from 7 to 9 carbon atoms. Thus, in this embodiment, the same solvent may be employed in the liquid/liquid extraction step and the subsequent extractive distillation of the butylene oxide-containing organic phase recovered in the first step. Solvent is recovered for reuse in both the liquid/liquid extraction step and the solvent extraction step by fractionation of the solvent extraction column bottoms.

The molar ratio of extractive distillation solvent added in the second, extractive distillation stage to butylene oxide present in organic phase recovered from the first, liquid/liquid extraction stage may vary broadly from about 2 to 15:1, although the preferred ratio is from about 3 to 6:1.

This invention is illustrated by the following examples.

EXAMPLE 1

A crude 1,2-butylene oxide stream having the composition shown in Table I is mixed with n-octane in an extractor (i.e., an agitated vessel) maintained at a temperature of 90° F. and at about atmospheric pressure. The molar ratio of n-octane:butylene oxide is about 1:1. Feed/solvent mixture is withdrawn from the extractor and is introduced into a decanter maintained under quiescent conditions, wherein two phases form and are recovered: an aqueous raffinate and an organic extract. Compositions of the raffinate and extract are indicated in Table I Increasing the molar ratio of n-octane:butylene oxide to 2:1 increases water removal from the butylene oxide-rich organic phase to 90%. Further increases in the relative amount of n-octane added to the extractor were found to have no significant effect on water removal.

TABLE I

| | Stream Compositions (moles/hour) | | |
|---|---|---|---|
| Component | Crude Feed | Raffinate | Extract |
| Butylene oxides | 103 | 0.00 | 103 |
| n-octane | 0.0 | — | 104.3 |
| Water | 13.97 | 10.48 | 3.97 |
| Methanol | 1.17 | 0.33 | 0.84 |
| Acetone | 2.18 | 0.04 | 2.14 |
| Methyl acetate | 0.78 | 0.00 | 0.78 |
| Ethyl acetate | 0.32 | 0.00 | 0.32 |
| Methyl ethyl ketone | 0.20 | 0.00 | 0.20 |

EXAMPLE 2

In this example, the organic extract having the composition shown in Table I is subjected to extractive distillation in the presence of added n-octane solvent. The extract is introduced at a temperature of 100° F. and a pressure of 30 psia at the 15th theoretical plate of an extractive distillation column having 25 theoretical plates. A stream of n-octane at 150° F. is introduced at the top of the column. The molar ratio of added n-octane:butylene oxide present in the extract is maintained at about 4:1. An overhead stream having the composition indicated in Table II is withdrawn from the top of the column at a temperature of 187° F. and a pressure of 20 psia. A bottoms stream having the composition indicated in Table II is withdrawn from the bottom of the column at a temperature of 232° F. and a pressure of 24 psia.

TABLE II

| | Extractive Distillation Products (moles/hour) | | |
|---|---|---|---|
| Component | Extract Feed | Overhead | Bottoms |
| Butylene oxides | 74.91 | 0.52 | 44.39 |
| n-Octane | 45.47 | 0.90 | 218.97 |
| Water | 1.52 | 1.52 | 0.00 |
| Methanol | 0.37 | 0.37 | 0.00 |
| Acetone | 0.93 | 0.92 | 0.01 |
| Methyl acetate | 0.34 | 0.26 | 0.08 |
| Ethyl acetate | 0.14 | 0.00 | 0.014 |
| Methyl ethyl ketone | 0.09 | 0.00 | 0.09 |

Compared to extractive distillation of crude butylene oxides without the preceding liquid extraction step, the combined process embodiment exemplified above requires less solvent, steam and cooling water. The liquid extraction method of this invention is thus an attractive way to reduce operating costs for the removal of water and lower-boiling oxygenated impurities from crude butylene oxides.

What is claimed is:

1. A process for removing water from crude butylene oxides which comprises liquid extraction of a water-containing, crude butylene oxide with a solvent consisting essentially of acyclic, paraffinic hydrocarbons having from 7 to 9 carbon atoms to remove water in an aqueous raffinate and recovering an organic extract comprising butylene oxide and solvent.

2. The method of claim 1 wherein said solvent consists essentially of a straight chain hydrocarbon.

3. The method of claim 2 wherein said solvent consists essentially of n-octane.

4. The method of claims 1 or 3 wherein the solvent: butylene oxide molar ratio is within the range from about 1 to 4:1.

5. The methods of claim 4 wherein the solvent: butylene oxide molar ratio is within the range from about 1 to 2:1.

6. The method of claim 1 comprising the further step of extractively distilling the recovered organic extract in the presence of an added extractive distillation solvent consisting essentially of acyclic, paraffinic hydrocarbons having from 7 to 9 carbon atoms to remove impurities comprising water, methanol and acetone as distillate and recovering a bottoms stream comprising butylene oxide and solvent.

7. The method of claim 6 wherein the same solvent is employed in the liquid extraction and extractive distillation steps.

8. The method of claim 7 wherein the solvent consists essentially of n-octane.

* * * * *